(12) United States Patent
Bergethon

(10) Patent No.: US 7,024,238 B2
(45) Date of Patent: Apr. 4, 2006

(54) DETECTING ISCHEMIA

(75) Inventor: Peter Bergethon, Dover, MA (US)

(73) Assignee: New England Medical Center Hospitals, Inc., Boston, MA (US)

( * ) Notice: Subject to any disclaimer, the term of this patent is extended or adjusted under 35 U.S.C. 154(b) by 0 days.

(21) Appl. No.: 10/826,870

(22) Filed: Apr. 16, 2004

(65) Prior Publication Data

US 2004/0267153 A1    Dec. 30, 2004

Related U.S. Application Data

(60) Provisional application No. 60/463,190, filed on Apr. 16, 2003.

(51) Int. Cl.
*A61B 5/00* (2006.01)

(52) U.S. Cl. .................. 600/544; 600/545; 600/300

(58) Field of Classification Search ............... 600/300
See application file for complete search history.

(56) References Cited

U.S. PATENT DOCUMENTS

| | | | | |
|---|---|---|---|---|
| 6,052,619 | A * | 4/2000 | John ........................ | 600/544 |
| 6,516,214 | B1 * | 2/2003 | Boas ........................ | 600/431 |
| 6,551,252 | B1 * | 4/2003 | Sackner et al. ........... | 600/536 |

OTHER PUBLICATIONS

Carney et al., "Near-Infrared Spectrophotometric Monitori'ng of Stroke-Related Changes in the Protein and Lipid Composition of Whole Gerbil Brains," Anal. Chem., 65:1305-1313 (1993).

Chen et al., "Localizing the Focus of Ischemic Stroke with Near Infrared Spectroscopy," Chinese Medical Journal, 115: 84-88 (2002).

Delpy et al., "Estimation of Optical Pathlength Through Tissue From Direct Time of Flight Measurement," Phys. Med. Biol., 33:1433-1442 (1998).

Gardill et al., "Multichannel Derived Median Nerve SEP Compared to EEG in Patients With Vascular Cerebral Lesions," Electromyogr. Clin. Neurophysiol., 41:215-223 (2001).

Kandel et al., Principles of Neural Science, $3^{rd}$ Ed. Appleton & Lange, Norwalk, CT. (1991) (Table of Contents).

Kuroda et al., "Near-Infrared Monitoring of Cerebral Oxygenation State During Carotid Endarterectomy," Surg. Neurol., 45:450-458 (1996).

Lam et al., "Monitoring Electrophysiologic Function During Carotid Endarterectomy: A Comparison of Somatosensory Evoked Potentials and Conventional Electroencephalogram," Anesthesiology, 75:15-21 (1991).

(Continued)

*Primary Examiner*—Robert L. Nasser
(74) *Attorney, Agent, or Firm*—Fish & Richardson P.C.

(57) ABSTRACT

In one aspect, a method of detecting ischemia within the brain of a patient. The method includes assigning a first value to a first signal generated by a tissue on the right-hand side of the body and assigning a second value to a second signal generated by a tissue on the left-hand side of the body. The method also includes comparing the first value and the second value. The difference between the first value and the second value indicates that ischemia is present within the patient's brain.

54 Claims, 8 Drawing Sheets

OTHER PUBLICATIONS

Lanier, "Cerebral Function Monitoring During Carotid Endarterectomy," J. Neurosurgical Anesthesiology, 1:207-210 (1989).

MacDonell et al., "A Comparison of Somatosensory Evoked and Motor Evoked Potentials in Stroke," Ann. Neurol., 25: 68-73 (1989).

Manninen et al., "Somatosensory Evoked Potential Monitoring During Carotid Endarterectomy in Patients with a Stroke," Anesth. Analg., 93:39-44 (2001).

Meyer et al., "Somatosensory Evoked Potentials as a Measure of Experimental Cerebral Ischemia," J. Neurosurg., 62:269 (1985).

Nuwer et al., "IFCN Recommended Standards for Short Latency Somatosensory Evoked Potentials Report of an IFCN Committee," Electroencephalography and Clinical Neurophysiology, 91:6-11 (1994).

Ohba et al., "Changes of Motor Evoked Potentials in Global and Focal Ischemic Models of Cats," Hiroshima J. Med. Sci., 44:1-5 (1995).

Patton et al., "Single- and Multiple-Unit Analysis of Cortical Stage of Pyramidal Tract Activation," Journal of Neurophysiology, 17:345-363 (1954).

Terao et al., "Basic Mechanisms of TMS," Journal of Clinical Neurophysiology, 19:322-343 (2002).

* cited by examiner

DETECTING ISCHEMIA

RELATED APPLICATIONS

This application claims the benefit of U.S. Provisional Application No. 60/463,190, filed Apr. 16, 2003, the entire contents of which are hereby incorporated by reference herein.

TECHNICAL FIELD

This application relates to medical instruments and, more particularly, to medical devices that assess physiological parameters, including those that indicate the presence of an ischemic region within a biological tissue such as the brain.

BACKGROUND

Cerebrovascular diseases are among the leading causes of mortality and morbidity. Patients who experience a cerebrovascular accident, more commonly known as a "stroke," may experience either a gradual or an abrupt impairment of brain function, which is caused by a disruption of blood flow to (or within) the brain. Diseases that affect the arterial walls of blood vessels can lead to occlusions or partial occlusions (stenosis) that diminish blood supply. One of the most common arterial diseases is atherosclerosis, and when this condition is complicated by thrombosis or embolism, it is a frequent cause of stroke.

In some cases, stroke is associated with heart disease. Where stroke is caused by heart disease, it is typically due to embolism of thrombotic material that forms on the atrial or ventricular walls of the heart or on the valves on the heart's left side. This thrombotic material can detach and move as an embolus through the arterial circulation. Emboli can occlude arteries, including the larger arteries, in the brain. The most common causes of such "cardioembolic" stroke are nonrheumatic (non-valvular) atrial fibrillation (AE), prosthetic valves, rheumatic heart disease (RHD), ischemic cardiomyopathy, congestive heart failure, myocardial infarction, and protruding aortic arch atheroma (AAA). Patients recovering from surgery are also more prone to cardioembolic stroke. The disorders described here are treated in different ways, including with drugs and surgery (e.g., carotid endarterectomy). Where the patient has an occlusive disease, they may undergo carotid angioplasty or receive a carotid stent.

While angioplasty, carotid stenting, and other procedures (such as endarterectomy) target the opening of occluded arteries, they do not prevent new plaques from forming. Moreover, these treatments only provide a solution to localized problems; they do not prevent proximal embolic sources. For example, an embolus formed at a remote site (e.g., within the heart or ascending aorta) may still pass through a reopened stenosis in the carotid artery and occlude smaller arteries in the brain. This is a significant problem because about one-third of patients suffering from carotid occlusion also have proximal embolic sources. Similarly, endarterectomy is not suitable for intracranial arteries or those in the vertebrobasilar system since these arteries are positioned within environments that do not lend themselves easily to surgical procedures (brain tissue and bone tissue) or are very small in diameter.

While stroke has been recognized as a leading cause of death, many stroke victims survive with substantial long-term disability. Their disabilities may be manifest as physical impairment due to motor weakness and lack of coordination, as a cognitive impairment including derangement in planning and executing complex tasks, or both. While some recovery is usually possible, victims of severe strokes often remain debilitated for the remainder of their lives.

SUMMARY

Until recently, physicians were rarely able to successfully limit the ischemic damage caused by a disruption of blood flow to the brain; neurons (information-carrying cells within the brain) are especially sensitive to oxygen deprivation, being killed or severely damaged when their blood supply is disrupted for even a short period of time. It has now been shown, however, that administration of tissue plasminogen activator (tPA), beginning within about three hours after the onset of the stroke, can reduce morbidity. With the development of this treatment, it has become more important than ever before to be able to identify potential stroke victims in a timely manner. More generally, whether a patient is a candidate for treatment with tPA or not, if they may be experiencing a stroke, prompt medical attention is advisable. Accordingly, the present invention provides systems and methods for detecting ischemic tissue (tissue damaged by lack of oxygen) within a patient's brain (e.g., within the left or right hemisphere of the brain).

While some of the possible advantages associated with the invention will be apparent from the description below, we note here that, as the components of the present systems can be physically compact, the systems are suitable for use in the field by emergency medical personnel, and they may be readily transported within a hospital or other facility (e.g., a nursing home). Similarly, we note from the outset that, while human patients may certainly be subjected to the methods described herein, the invention is not so limited. For example, the systems and methods of the present invention can be used to assess ischemia in domesticated animals and in the course of testing therapeutic agents (e.g., new thrombolytic agents) in animal models or ex vivo organ systems.

In one aspect, the invention features methods of determining ischemia. For example, using the methods of the present invention, one can determine whether a biological tissue (e.g., brain tissue) contains ischemic tissue and, optionally, the approximate location and apparent extent of the ischemia. As patients who experience a stroke tend to experience inadequate oxygen supply on only one side of the brain (the left hemisphere and the right hemisphere have largely independent vascular networks), the methods of the invention can be carried out by assessing signals generated by each side of the brain. In one embodiment, the method includes generating a final value from (a) a first signal received from a location or region on a first side of the patient's body (e.g., a signal from the left hemisphere of the brain) and (b) a second signal received from a location or region on a second side of the patient's body (e.g., a signal from the right hemisphere of the brain). The locations or regions on the first and second sides of the body may be opposite (or roughly opposite) one another, and we may refer to these sides below as being on the "lateral" and "contralateral" sides of the patient's body (e.g., responses may be recorded from electrodes placed over the left and right parietal cortex). In a subsequent step, the method includes determining, based on the final value, whether ischemia is present, or likely to be present, in the patient's brain (particularly the unilateral ischemia typically seen in the event of stroke). For example, the invention features methods of detecting ischemia within the brain by assigning a first value to a signal generated (directly or indirectly) by a first side of the brain, assigning a second value to a signal generated by a second side of the brain, and comparing the first value and the second value. The comparison can give rise to the final value. A signal is generated directly by the brain when it is manifest in brain tissue per se (e.g., electrical activity within the brain). A signal is generated indirectly when it is manifest in a tissue controlled by the brain (e.g., a muscle or other peripheral structure).

As the comparison is of one value to another, it may be expressed as a fraction or ratio. For example, where the lateral and contralateral sides of the brain generate equivalent signals, preferably under the same or equivalent circumstances, the ratio will be about 1:1. A difference between the first signal and the second signal will produce a ratio other than 1:1 (and/or a generated final value other than about 1.0), indicating that ischemia is present within the tissue (e.g., within at least one hemisphere of the brain). The larger the ratio (and/or the further the generated final value from 1.0), the more likely that ischemia is present.

Stimuli can be applied to, and responses analyzed from, different regions of the brain. For example, one can position components of the present system to stimulate or record from regions of the brain supplied by different blood vessels (e.g., the vascular regions supplied by the middle cerebral artery (MCA), anterior cerebral artery (ACA), and/or posterior cerebral artery (PCA)). The stimulators and detectors (e.g., electrodes, magnets, photodiode detectors and the like) described in connection with any embodiment of the invention (e.g., a method or system in which SSEPs are recorded from the patient's brain or NIRS-based methods and systems) can be variously placed over different regions of the brain to roughly map the affected regions (e.g., those affected by ischemia due to occlusion or hemorrhage from the ACA, MCA, or PCA). If necessary or desired, this information can be supplemented by subjecting the patient to an imaging technique (such as an x-ray or magnetic resonance imaging).

One of ordinary skill in the art will recognize that, even within a healthy patient, there may naturally be some difference in the signals generated by the two sides of the brain. Thus, insignificant differences (e.g., differences that are not significant based on the Student's t test with "p" set at an accepted value (e.g., $p<0.01$)) may be ignored. As stroke tends to be a progressive disorder, any patient who continues to exhibit or complain of distress can be assessed repeatedly; differences that were insignificant earlier may become significant with time. Accordingly, the methods of the invention can be used, alone or in combination with other tests, to diagnose a stroke; to monitor the progression of the stroke; to evaluate a patient's response to medical treatment once stroke is suspected (e.g., administration of tPA, a growth factor, an anti-apoptotic agent or other neuroprotective agent or therapy); to monitor a patient during surgery or other physiologically stressful event (particularly a surgery or event that places a part of a somatosensory pathway at risk); and/or to select a treatment regime (for example, a patient experiencing a hemorrhagic stroke, where blood vessels are broken, rather than occluded, should not receive thrombolytic agents).

The signal assessed can be any detectable signal generated by the brain. For example, the signal can be an electrical signal (detected, for example, by electroencephalography), a mechanical signal (detected, for example, by muscle movement), or a chemical or metabolic signal (e.g., the concentration of hemoglobin (e.g., the relative amounts of oxyhemoglobin (HbO) and deoxyhemoglobin (Hb)). A mechanical signal (e.g., muscle movement or other brain-driven event) is an example of an "indirect" signal, as it is a consequence of (or a reflection of) brain activity.

To assess electrical activity, one can record evoked potentials, such as somatosensory evoked potentials (SSEPs). The brain generates these signals in response to sensory stimuli (i.e., a stimulus to the auditory, visual, or olfactory systems or a stimulus to the skin or taste buds). More specifically, SSEPs include a series of waves that reflect the sequential activation of neural structures along a somatosensory pathway (e.g., activation by stimulation of a peripheral nerve). In the context of the present invention, SSEPs can be elicited by stimulating, for example, the median nerve at the wrist, the ulnar nerve at the arm, the common peroneal nerve at the knee, and/or the posterior tibial nerve at the ankle and recorded from electrodes placed over the scalp, spine, and/or peripheral nerves. In accordance with the methods of the invention, one can assess SSEPs (e.g., their amplitude or latency) generated by the first and second sides of the brain by, for example, recording over the lateral and contralateral sides of the patient's skull. The recording can be made after the patient receives a bilateral and essentially equivalent stimulus (e.g., after stimulating both eyes with light and/or both ears with sound; alternatively, or in addition, after stimulating lateral and contralateral peripheral nerves, such as those mentioned above).

More specifically, in one embodiment, the method includes generating a final value from (a) a first SSEP received from a first side of the patient's brain and (b) a second SSEP received from a second side of the patient's brain. Ischemia is likely to be present where the final value indicates that there is a difference in the capacity of the two hemispheres to respond to sensory input. As noted above, one can arrive at a final value by comparing signal from a first side of the tissue (here, an SSEP generated within one hemisphere of the brain) with the signal from a second side of the tissue (here, an SSEP generated within the contralateral hemisphere of the brain). Where a comparison of the SSEPs from the two hemispheres of the brain establishes an inequality (as demonstrated, for example, by failure to conform to a ratio of about 1:1), ischemia is likely to be present.

To assess a mechanical signal, each side of the brain can be stimulated to bilaterally activate muscle fibers (within a single muscle or group of muscles). For example, the brain can be stimulated by the procedure known as transcranial magnetic stimulation (TMS), which is presently used to treat depression and for cortical mapping studies. A magnet or electromagnetic coil can be held near or against the scalp; magnetic pulses passing through the skull induce an electric current that alters the activity of nerve cells to such an extent that an efferent signal causes a measurable movement in a muscle (or muscle group). For example, one can measure the force of the muscular response or its latency. Accordingly, the invention provides methods of detecting ischemia by generating a final value from (a) a TMS-evoked movement of muscle fibers on one side of the body and (b) a TMS-evoked movement of muscle fibers on the other side of the body and determining whether the final value indicates that ischemia is present within the brain. For example, one can apply TMS, simultaneously or sequentially, to the left and right sides of the brain (preferably the stimulation to each side is equal or comparable) and record the amplitude or latency of contraction in the stimulated muscle(s) on each side of the body. Where a comparison of the contractions (i.e., the contractions on the left and right sides of the body)

establishes an inequality (as demonstrated, for example, by failure to conform to a ratio of about 1:1), ischemia is, or is likely to be, present.

To assess a chemical or metabolic signal, the methods of the invention can include near-infrared spectrometry (NIRS) to assess changes in the concentrations of molecules within the brain, such as lipids (e.g., HDL, LDL, and cholesterol), proteins, and hemoglobin. For example, one can assess the concentrations of HbO and Hb in each hemisphere of the brain using a technique such as NIRS (see Carney et al., Anal. Chem. 65:1305–1313, 1993). NIRS provides chemical "imaging" by utilizing light in the near infrared range (about 700–1000 nm (e.g., 650–950 nm) to assess, for example, cerebral oxygenation. The instrument employed includes fiberoptic bundles (or "optodes"), which can be placed on opposite sides of the head (e.g., over the parietal cortex). Accordingly, the invention provides methods of detecting ischemia by generating a final value from (a) an amount or concentration of one or more molecules (e.g., HbO and/or Hb) expressed in one hemisphere of the brain and (b) an amount or concentration of that same type of molecule (or those same types of molecules) in the other hemisphere of the brain. For example, one can apply NIRS, simultaneously or sequentially, to the left and right sides of the brain and record the amount(s) or concentration(s) of one or more molecules within the two sides of the brain. Like oxygen and various forms of hemoglobin, the molecules should be within a family or class affected by oxygen deprivation. Where a comparison of the amount(s) or concentration(s) (i.e., the amounts or concentrations on the left and right sides of the brain) establishes an inequality (as demonstrated, for example, by failure to conform to a ratio of about 1:1), ischemia is, or is likely to be, present.

In more specific embodiments, the invention features methods of assessing (e.g., detecting, mapping, or determining the extent of) ischemia within a brain of a patient by providing (e.g., obtaining, assigning, or generating) a first value to a first signal generated by a tissue on the right-hand side of the body and a second signal generated by a tissue on the left-hand side of the body and comparing the first value and the second value. The signals generated are physiological signals that change in the event of ischemia. Thus, a difference between the first value and the second value indicates that ischemia is present within the brain. The methods can further include applying a first stimulus to the left-hand side of the body; receiving the first signal in response to the first stimulus; applying a second stimulus to the right-hand side of the body; and receiving the second signal in response to the second stimulus. As noted above, the stimuli can be an electrical stimulus or (e.g., an electrical current) a stimulus that stimulates a sensory organ (e.g., a audible, visual, or audiovisual stimulus can be supplied to the patient's ears, eyes, or both), or a mechanical stimulus (e.g., pressure or mild pain (e.g., as felt when pricked with a pin). Electrical or mechanical stimuli can be used to stimulate the patient's skin or an underlying muscle. More specifically, the first stimulus can be applied to a sensory organ on the left-hand side of the body and the first signal can be generated by the right hemisphere of the brain. Alternatively, or in addition, the second stimulus can be applied to a sensory organ on the right-hand side of the body and the second signal can be generated by the left hemisphere of the brain. With respect to the detectable signal, the first electrical signal can be a first somatosensory evoked potential (SSEP) and the second signal can be a second SSEP. Moreover, one can evaluate any parameter associated with the SSEP (e.g., amplitude, frequency or latency).

Rather than stimulating a peripheral tissue and recording a response from the brain, one can stimulate the brain and record a response from a peripheral tissue. Thus, in the methods of the invention, the first stimulus (e.g., an electrical, magnetic, or electromagnetic stimulus) can be applied, for example, to the left hemisphere of the brain and the first signal is generated by a muscle on the right-hand side of the body. Alternatively, or in addition, the second stimulus (e.g., an electrical magnetic, or electromagnetic stimulus) can be applied to the right hemisphere of the brain and the second signal can be generated by a muscle on the left-hand side of the brain. Regardless of the exact nature of the stimulus, it is preferably applied equally, or roughly equally, to both sides of the patient's body. The signal can be a muscular contraction (as evidence, for example, by a change in the charge potential of a muscle fiber or group of muscle fibers, a motor unit potential, or a physical contraction). The signal can be assessed by any of its parameters (including amplitude (e.g., force) or latency).

The invention also features systems that can be used to carry out the methods described herein. For example, in one aspect, the invention features an article that includes a machine-readable medium that stores executable instructions for assessing ischemia. The instructions cause a machine to generate a final value from (a) a first signal received, directly or indirectly, from a location or region on a first side of the patient's body (e.g., the left hemisphere of the patient's brain) and (b) a second signal received, directly or indirectly, from a location or region on a second side of the patient's body (e.g., the right hemisphere of the patient's brain). Where the locations or regions are roughly symmetrical around the midline, they can be described as being on the lateral and contralateral sides of the patient's body. The instructions also cause the machine to determine ischemia in the patient based on the final value. As with the methods described above, the instructions, when executed and the outcome is displayed (on the article or on an attached or remotely controlled indicator), allow one to determine whether ischemia is, or is likely to be, present within a patient's brain; the approximate location of the ischemic tissue; and/or the apparent extent of the ischemia.

More specifically, the systems of the invention can include an apparatus such as a computer that includes a memory that stores executable instructions for assessing ischemia. The apparatus can include a processor for executing the instructions and generating a final value from any of the types of signals described above. The apparatus can receive input directly or indirectly from a patient. In accordance with the methods described above, the input can include data generated by, or collected from, a location or region on a first side of the patient's body (e.g., the left hemisphere of the patient's brain) and a location or region on a second side of the patient's body (e.g., the right hemisphere of the patient's brain). The locations or regions, as noted above, may be approximately symmetrical around the patient's midline, and the input can include information about any detectable signal generated by the brain (e.g., the input can include any of the electrical, mechanical, or chemical (or metabolic) signals described above). Where necessary or desired, the input can be processed by a signal amplification and conversion (SAC) device that may include one or more filters and/or an amplifier or analog-to-digital (A/D) converter.

The apparatus may be attached to (physically or electronically linked to) a stimulator that stimulates the patient in one or more of the ways described above (e.g., by Other features,

DETAILED DESCRIPTION

Figure 1:
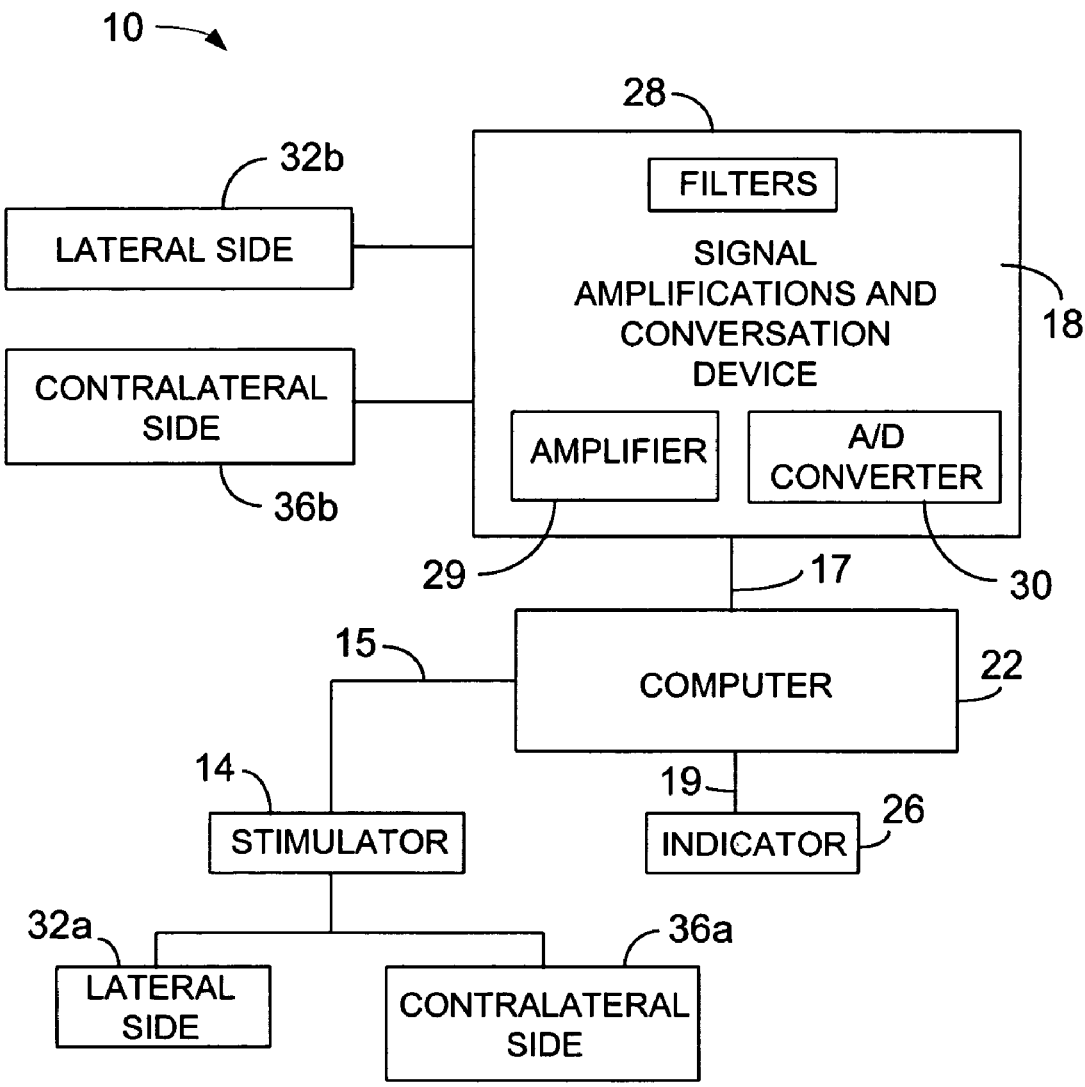
FIG. 1 is a block diagram of a system for detecting ischemia.

Referring to FIG. 1, an ischemia detection system 10, using a process 40 (see FIG. 2), can assess ischemia in a subject (e.g., a human, domesticated animal, or laboratory animal; we may refer to the subject as a "patient" even though they may be healthy or apparently healthy). System 10 includes a stimulator 14, a SAC device 18, a computer 22, and an indicator 26.

Directly stimulating one type of tissue on opposing sides of the body and recording a response from a different type of tissue, also on opposing sides of the body, provides information that can be processed to assess ischemia within the brain. As in system 10, tissues directly stimulated on the lateral 32a and contralateral 36a sides of the patient can be tissues within the left and right hemispheres of the brain, in which case the responding tissues on the lateral 32b and contralateral 36b sides of the patient are peripheral (non-brain) tissues, and vice-versa: where tissues directly stimulated on the lateral 32a and contralateral 36a sides of the patient are peripheral (non-brain) tissues, the responding tissues on the lateral 32b and contralateral 36b sides of the patient are tissues within the left and right hemispheres of the brain. One of ordinary skill in the art will understand that numerous specific configurations within the two broadly described here are possible. As the brain receives signals from, and sends signals to, the peripheral tissues, ischemia within the brain can be assessed either by assessing the brain's failure to respond to incoming signals or to propagate and convey signals to the periphery.

Stimulator 14 is configured to stimulate various locations on (or regions of) the patient's body, including, as noted above, regions of the central nervous system (CNS; e.g., the brain) or regions throughout the periphery (e.g., the skin, or other sensory organs on the arms, legs, torso, or face). Stimulator 14 stimulates a region 32a on one side of the patient's body and a region 36b on the other side of the patient's body that, preferably, are at least roughly symmetrical around the midline. Where the region is the brain, stimulator 14 may provide, for example, an electrical or magnetic stimulus (e.g., stimulator 14 can be a cortical stimulator 214 (see FIG. 6); where the region is a sensory organ, such as the eye, ear, nose, tongue, or skin, stimulator 14 may provide, for example, a visual, auditory, olfactory, gustatory, or mechanical (e.g., pressure or pain) stimulus, respectively, or a combination thereof. In system 10, stimulator 14 is connected to and controlled by computer 22 through a connector 15.

To assess ischemia, computer 22 receives input from various locations on (or regions of) the patient's body, including regions within the CNS (e.g., the brain) or regions throughout the periphery (e.g., muscle fibers). In system 10, input is received from lateral 32b and contralateral 36b sides of the subject's body. Input is conveyed by connectors 21a and 21b to SAC device 18, which includes filters 28, an amplifier 29, and an analog-to-digital (A/D) converter 29. Filters 28 remove undesirable portions of the input. Amplifier 29 amplifies the input (including noise and the like), and A/D converter 30 converts the amplified response signals from analog to digital, as required. SAC device 18 is connected to and controlled by computer 22 via a connector 17.

Computer 22 is connected to and controls indicator 26 via a connector 19. Indicator 26 produces, or includes, some signal (e.g., a text message, number, symbol, color, or the like) indicating whether or not ischemia is present.

Figure 2:
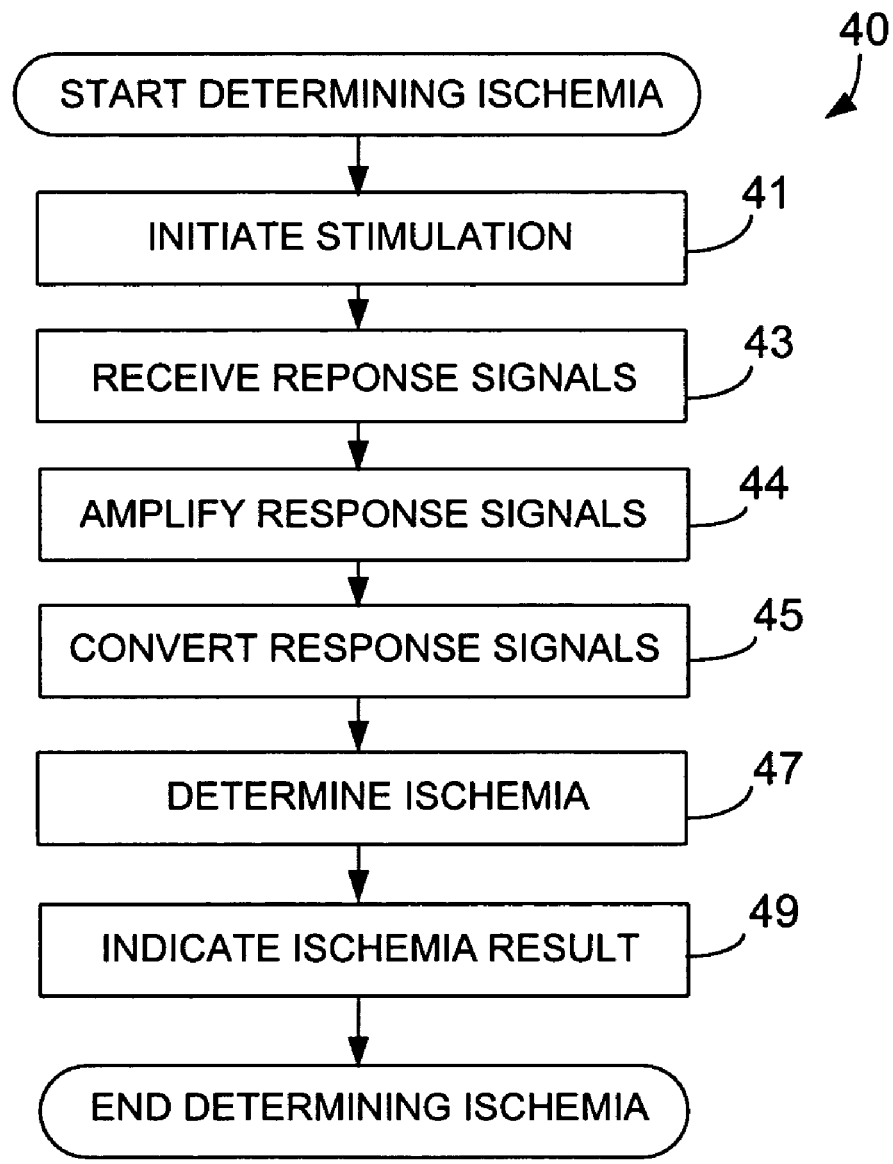
FIG. 2 is a flowchart of a process to detect ischemia.

Referring to FIG. 2, process 40 initiates (41) stimulation of tissue on lateral 32a and contralateral 36a sides of a patient's body using stimulator 14 for a predetermined period of time and at a predetermined intensity. Process 40 receives (43) response signals from tissues on lateral 32b and contralateral 36b sides of the body. For example, where process 40 initiates (41) stimulation of a peripheral sensory organ, SAC device 18 receives response signals from the left and right hemispheres of the brain (for example, SSEPs can be conveyed via connectors 21a and 21b from vascular regions supplied by the MCA, ACA, and/or PCA to SAC device 18). Process 40 amplifies (44) the response signals and converts (45) the response signals from analog to digital signals. Process 40 determines (47) whether ischemia is present in the patient's brain using subprocess 47 (see FIG. 4) to compare the response of the tissue on the lateral 32b and contralateral 36b sides of the body. For example, where stimulator 14 stimulates a peripheral nerve (e.g., the median, common peroneal, or posterior tibial nerve; or the optic, olfactory, or auditory nerve), SAC 18 receives input from the left and right hemispheres of the patient's brain. Similarly, where stimulator 14 stimulates the left and right hemispheres of the patient's brain (with, for example, a magnetic field), SAC 18 receives input from peripheral tissues on the left and right sides of the patient's body. Indicating ischemia (49) concludes process 40, which may be repeated over time or to test different regions of the patient's body.

Figure 3:
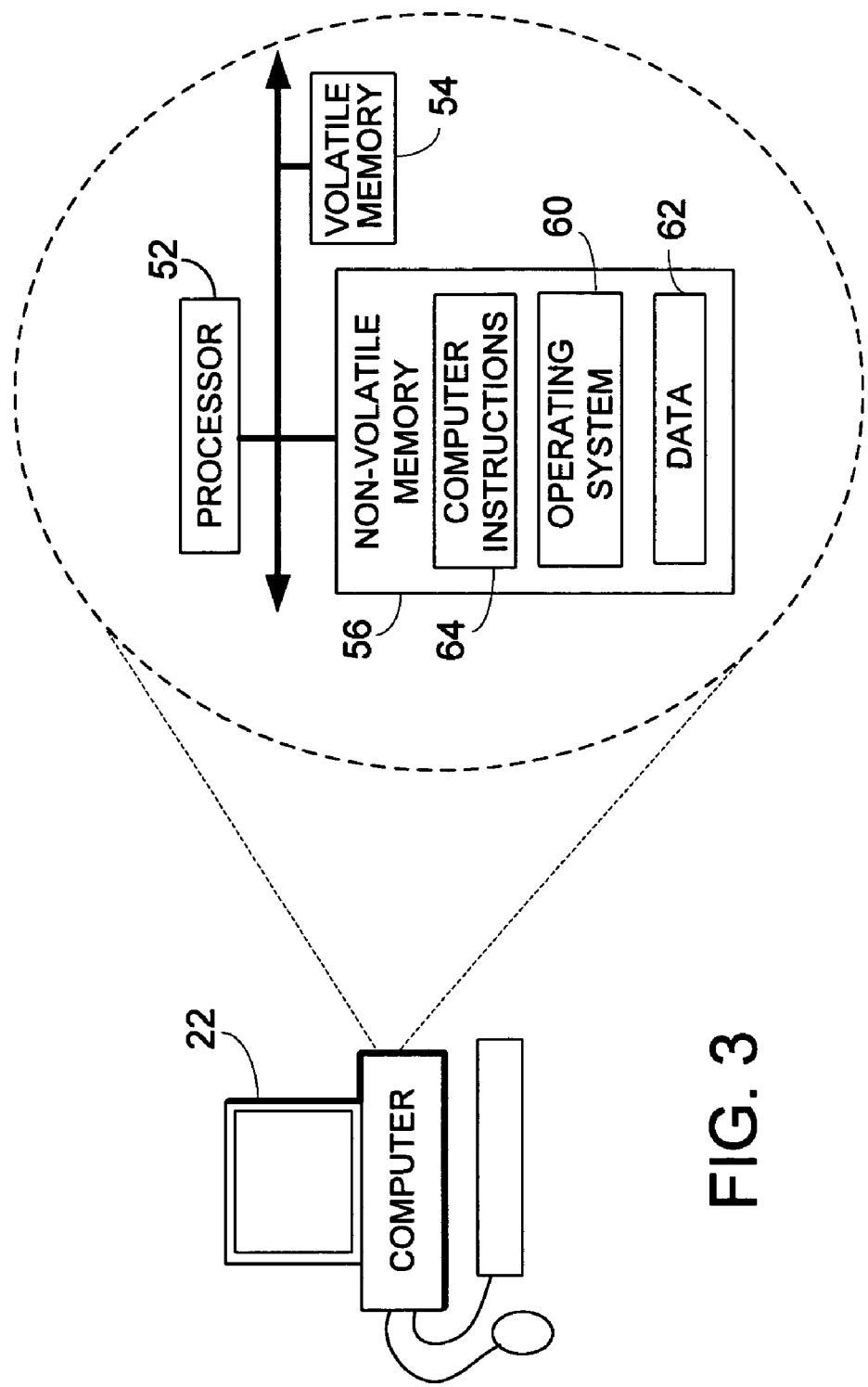
FIG. 3 is a block diagram of a computer system on which the process of FIG. 2 may be implemented.

Referring to FIG. 3, computer 22 determines the presence of ischemia in the patient's brain using process 40. Computer 22 includes a processor 52, a volatile memory 54, and a non-volatile memory 56 (e.g., a read only memory, flash memory, disk, or the like). Non-volatile memory 56 stores operating system 60, data 62 for determining ischemia (e.g., input or response measurements and, optionally, predetermined threshold values for ischemia), and computer instructions 64 that are executed by processor 52 out of volatile memory 54 to perform process 40. Indicator 26 receives results determined by computer 22 and indicates whether ischemia is present in the patient. For example, indicator 26 may be a computer monitor, a television screen, a cathode ray tube, an LCD or plasma screen, an oscilloscope, a paper printout, a chart recorder, and so forth that renders the results.

Figure 4:
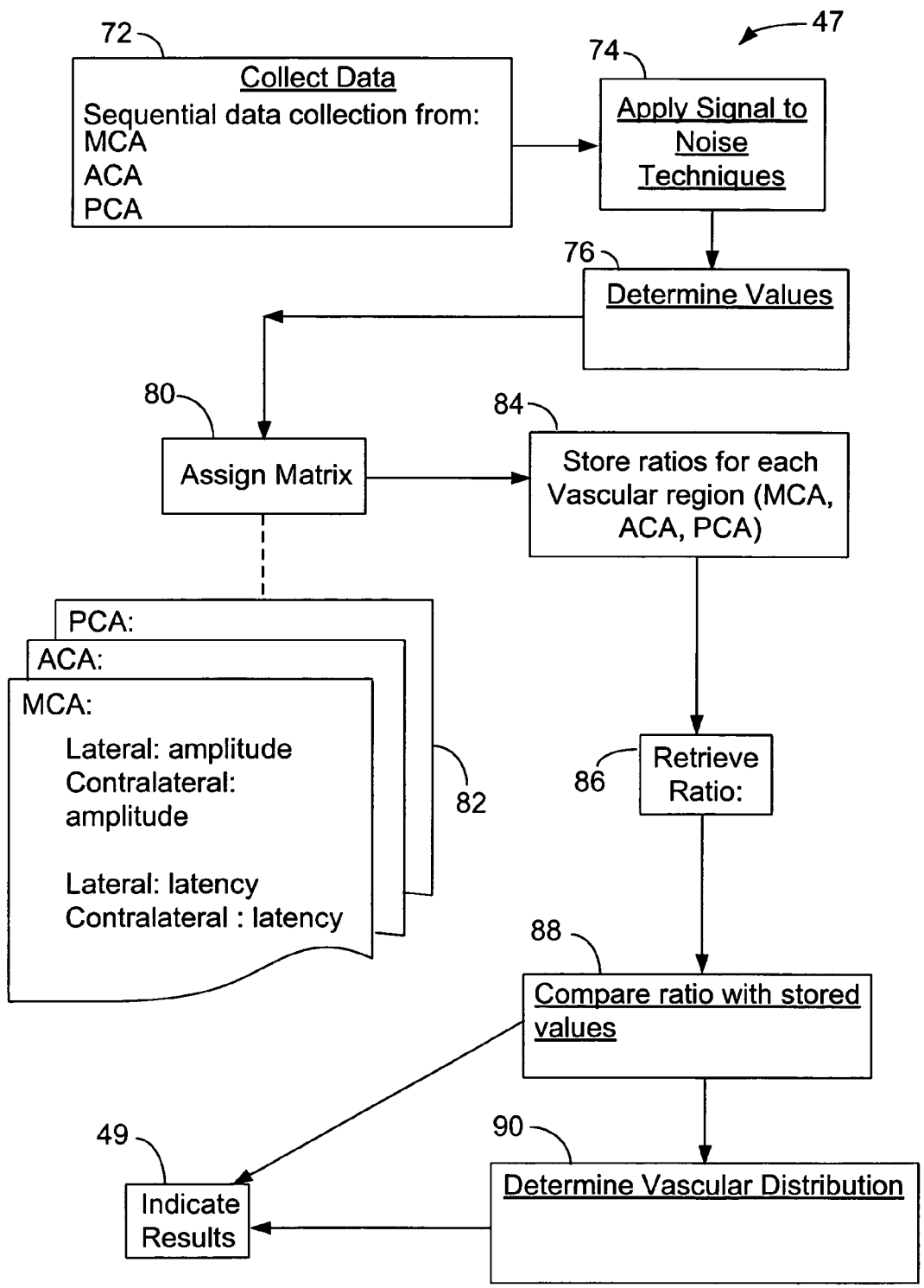
FIG. 4 is a flowchart of a subprocess of the process of FIG. 2.

Referring to FIG. 4, subprocess 47 collects (72) data received from each vascular region measured. For example, computer 22, sequentially or simultaneously, collects data from vascular regions supplied by the MCA, ACA, and/or PCA. Subprocess 47 adjusts (74) the signal-to-noise ratio within the response signals (for example, the sampled data may be averaged to enhance the signal-to-noise ratio); computer 22 can, for example, use averaging techniques on the response signals. Subprocess 47 determines (76) values for amplitude and/or latency of each response signal and assigns (80) the values to a matrix 82. Subprocess 47 stores (84) a ratio of values assigned to the amplitude and/or latency of the input from each vascular region on the lateral and contralateral sides of the patient. Subprocess 47 retrieves (86) the stored ratio(s) and compares (88) each ratio with a stored value. Subprocess 47 determines (90) whether ischemia is present in each vascular region based on the comparison. For example, computer 22 compares (88) the retrieved ratio with a stored value. If the retrieved ratio is different from the stored value, ischemia is present, or likely to be present, in the area from which the data was received. As described above, using alternative subprocesses, ischemia can be detected and assessed by comparing input received from a lateral side of the patient's body (e.g., the left hemisphere of the brain) with input received from the contralateral side of the patient's body (e.g., the right hemisphere of the brain). Where the inputs differ, the ratio generated will be greater than or less than about 1.0, and ischemia will exist in the patient.

Figure 5:
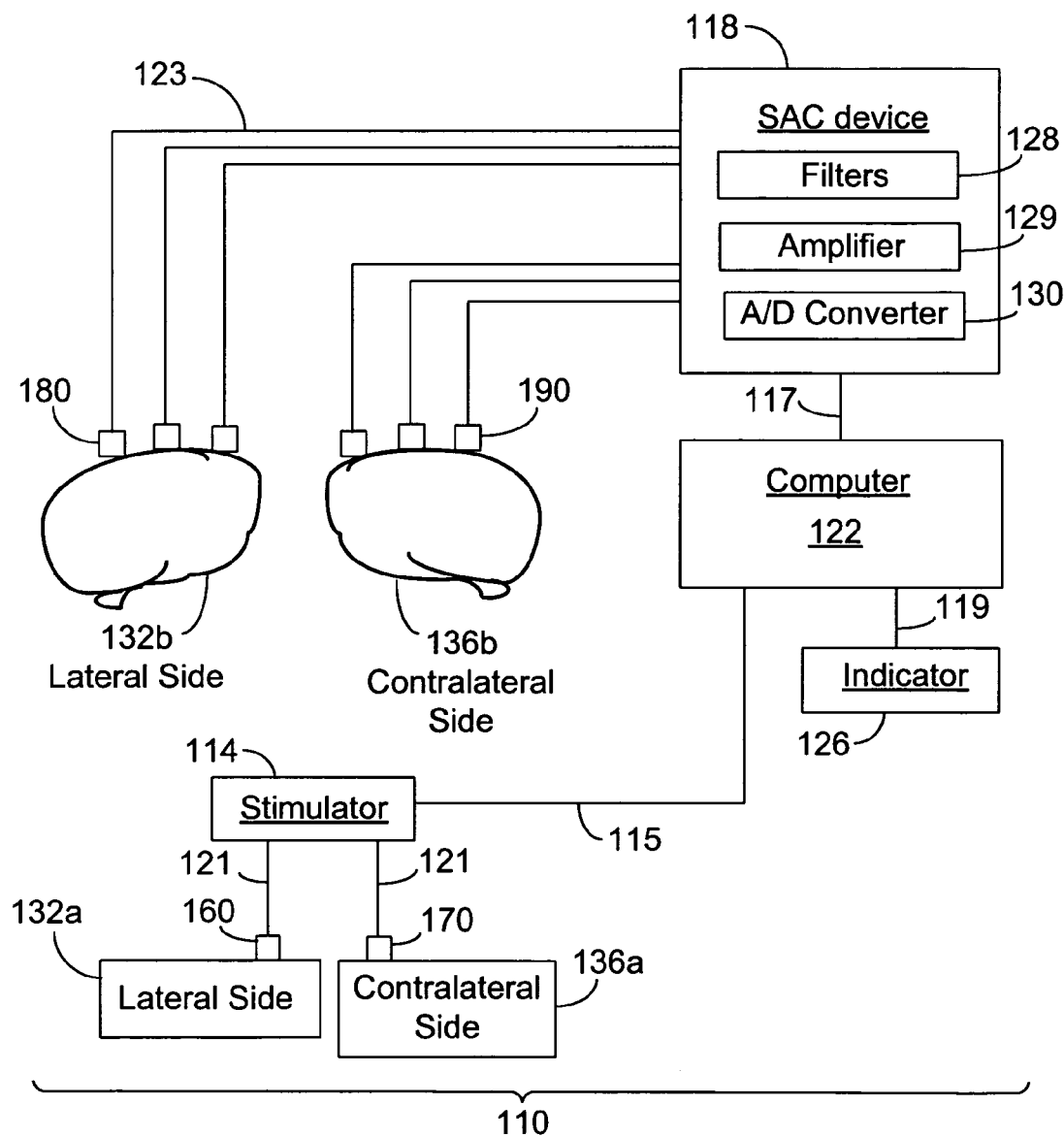
FIG. 5 is a block diagram of an exemplary system for assessing ischemia where SSEPs are recorded as an indication of electrical activity in the brain.
Figure 6:
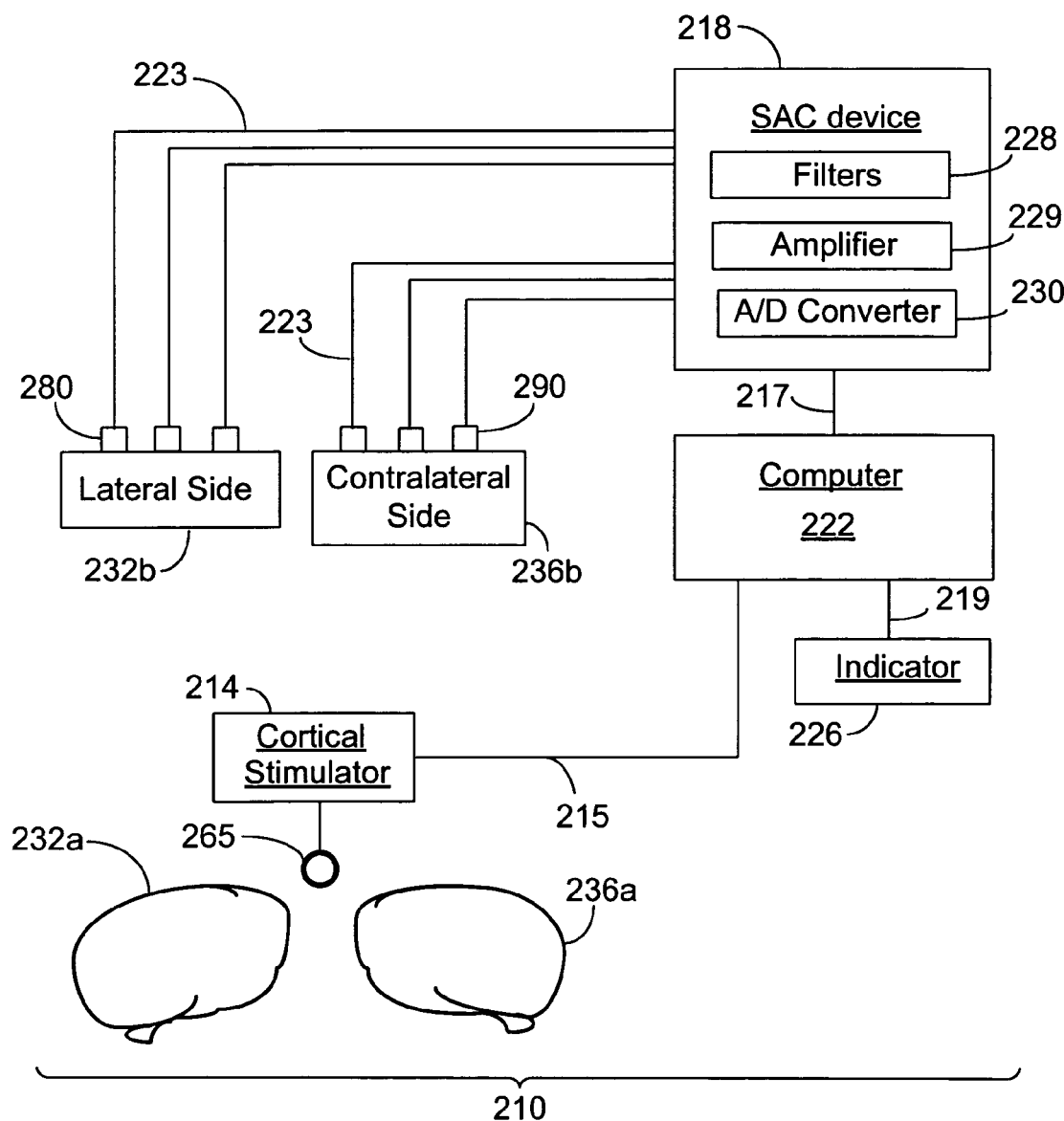
FIG. 6 is a block diagram of an exemplary system for assessing ischemia where muscular activity is recorded following TMS.
Figure 7:
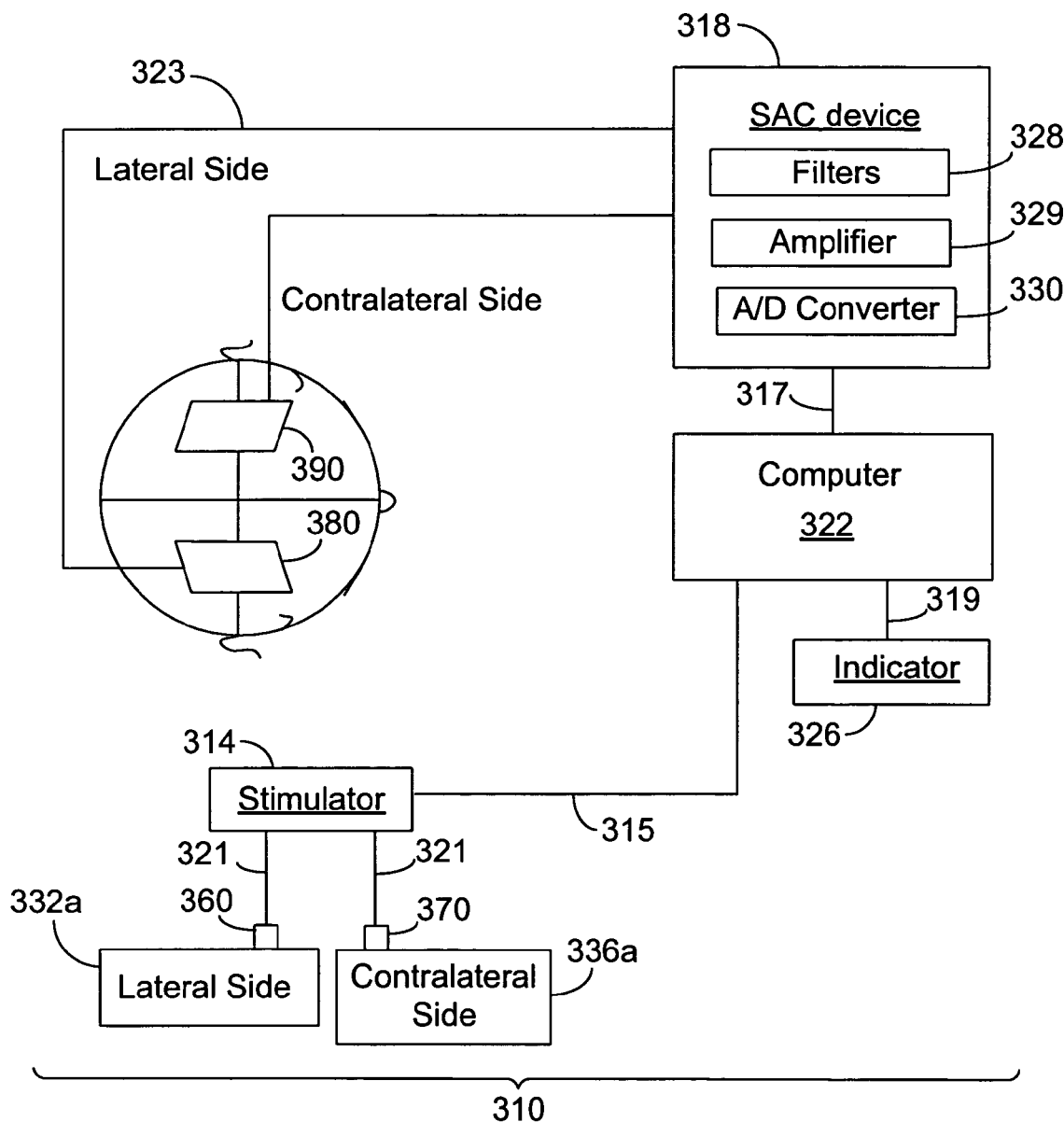
FIG. 7 is a block diagram of an exemplary system for assessing ischemia where NIRS is used to assess chemical or metabolic activity in the brain.

System 10 can be used to detect ischemia using a number of different techniques, some of which are illustrated in FIGS. 5, 6, and 7.

Assessing Ischemia with SSEPs: Referring to FIG. 5, ischemia detection system 110 detects and can assess ischemia based on measurements of SSEPs (using, for example, an EEG machine); SSEPs normally change in response to stimulation of an afferent sensory pathway. System 110 includes a stimulator 114, a SAC device 118, a computer 122, and an indicator 126.

Stimulator 114 is configured to stimulate a peripheral nerve fiber or bundle. The stimulating phenomenon can be an electrical stimulation (e.g., an electrical current), physical contact (e.g., pressure or a mildly painful stimulus), or an event perceived by another sense (e.g., an event perceptible by the eyes, ears, nose, or mouth). The lateral 132a and contralateral 136a sides each include a peripheral nerve that would normally convey the stimulus to the brain (e.g., the tibial, median, facial, trigeminal, ulnar, radial, eighth cranial nerve, or any other cranial nerve). Given the present understanding of the nervous system, one can more particularly select the region(s) to be stimulated and the area(s) for recordation. For example, stimulating the median nerve will provide information regarding the vascular field supplied by the MCA; stimulating the peroneal nerve will provide information regarding the vascular field supplied by the ACA; stimulating the eight cranial nerve (to elicit a brainstem auditory evoked response (BAER)) will provide information regarding the vascular field supplied by the PCA; and so forth. Thus, bilateral stimulation of the peroneal, median, and eighth cranial nerves can generate data that allows one to assess three vascular regions within both hemispheres of the brain.

Stimulator 114 delivers consistent, repeated stimulation (e.g., electrical stimulation) at a fixed but adjustable frequency, for a fixed but adjustable duration, and at a fixed but adjustable amplitude. While the exact characteristics of the stimulus will vary, the stimulus should be one that would normally be sufficient to stimulate a detectable signal from the brain. Preferably, comparable stimuli are applied to lateral 132a and contralateral 136a sides of the patient's body. For example, stimulator 114 delivers to lateral 132a and contralateral 136a sides of the patient's body an electrical stimulus of between about 5 and 60 mA (e.g., about 5–25, 5–30, 10–50, 35–55, or about 30 mA), for about 50 µs to 1 ms (e.g., about 50–500 µs or about 0.1, 0.2, 0.3, 0.4, 0.5, 0.6, 0.7, 0.8, or 0.9 ms), at a frequency of between about 0.1 and 100 Hz. For example, the patient may receive between about 2–10 stimuli per second (e.g., 5 stimuli per second). The stimulus will typically causes a 1 to 2 cm movement in the stimulated muscle (e.g., if the median nerve is stimulated, the stimulus causes a 1 to 2 cm movement in the thumb).

Stimulator 114 is connected via connectors 121, to stimulation electrodes 160 and 170, which are configured to deliver the electrical stimulus generated by the stimulator 114 to the lateral 132a and contralateral 136a areas of the patient's body and may be removably attached to the patient's skin in the area of the desired stimulation. Surface electrodes are commercially available from, for example, Grass-Telefactor (West Warwick, R.I.). Generally the electrical contact impedance at the electrode/skin interface is kept below 5000 Ω. Where the stimulus to be provided is auditory, electrodes 160 and 170 can be replaced with earpieces, headphones, or the like. Alternatively, where the stimulus is audible or visual, physical connectors can be omitted. Where a physical connection is required, connector 121 can be a coupling or adapter known in the art (e.g., a Bayonet Neill Concelman (BNC) connector, a banana jack, a phone connector, a D-shell connector, a cable connector, a coaxial connector, an alligator clamp, or the like; these couplers and adaptors are suitable for use with any of the connectors within system 110). Alternatively, the connector 121 can be permanently connected to either or both of the stimulator 114 and the electrodes 160 or 170 by a solder, or other electrically conductive weld known to those of skill in the art.

Alternatively, the stimuli can be delivered with a needle electrode rather than a surface electrode. Needle electrodes are known in the art and are commercially available. When used in the context of the present invention, the needles are preferably sterile and are placed in sufficient proximity to the nerve induce 1 to 2 cm of movement in the innervated muscle.

The response to stimulation is recorded from lateral 132b and contralateral 136b sides of the patient's brain via electrodes 180 and 190, respectively, which are connected via connectors 123 to SAC device 118. SAC device 118 measures, for example, an EEG waveform from the lateral 132b and contralateral 136b sides of the patient's brain. EEG electrodes 180 and 190 are attached to the patient's scalp (by, for example, an adhesive) and are known in the art and are commercially available (from, for example, Grass-Telefactor (West Warwick, R.I.). The recording electrodes 180 and 190 can be placed on the scalp, as indicated. For example, to measure SSEPs evoked from stimulation of the median nerve, the recording electrodes 180 and 190 can be placed bilaterally on the forehead. Alternatively, or in addition, the recording electrodes 180 and 190 can be placed elsewhere on the body. For example, to measure SSEPs evoked from stimulation of the median nerve, the electrodes can be placed over Erb's point bilaterally (located within the angle formed by the posterior border of the clavicular head of the sternocleidomastoid muscle and the clavicle, 2 to 3 cm above the clavicle) or the skin overlying the fifth to seventh cervical vertebrae. More generally, the recording electrodes 180 and 190 can be placed on the second and third digits, the axilla, over the cervical spine, or on the scalp overlying the sensory cortex; any position is permissible so long as it is one from which SSEPs can be reliably and accurately measured. Those of ordinary skill in the art will be able to select suitable positions, regardless of the tissues that are stimulated by the stimulator 114.

During recording of the SSEP waveform, filters 128 are set to between 10 and 30 Hz and between 2000 and 5000 Hz, with a recording duration of approximately 30 msec The EEG signal is filtered at between 30 Hz and 3 kHz, with a sampling duration of 10 ms. Typically, stimulation recording conditions include stimulation of between 20 mA to 55 mA, for a duration of about 0.1. ms at a frequency of 5 Hz. On average, between 128 and 2000 repetitive stimuli/SSEP recordings are obtained and then averaged by the computer 122, although as few as 2, 5, 10, or 30 samples may be recorded. The computer 122 compares the averaged SSEP amplitude or latency obtained from the lateral 132b and contralateral 136b sides of the patient's brain.

SAC device 118 is configured to provide at least<20 ms waveform sampling; to have at least four channel inputs for electrodes 180 and 190 (and may have up to 8, 16, 32, 64, or 128 inputs); to have analog or digital inputs and outputs; and be designed to be able to interface with other possible components of system 110 including computer 122, indicator 126, and stimulator 114. In particular, SAC device 118 includes an independently adjustable gain for each channel, adjustable to a maximum of 200,000 (with a minimum of 50), and includes band-pass filtering from 0.11 Hz to 6 Hz (although high cutoff frequency filtering may be as high as 100 Hz).

Amplifier 129 has the following specifications.
Input impedance: greater than 200 MΩ/25 pF;
Sensitivity: 2 μV/div to 10 mV/div in 12 steps;
High frequency filter: 100 Hz to 15 Hz in 8 steps, 6 dB octave;
Low frequency filter: 0.5 Hz to 500 Hz in 8 steps, 6 dB octave;
Notch filter: greater 30 dB down at 60 Hz;
common-mode rejection ratio (CMRR): greater than 100 dB at 60 Hz;
Noise: less than 1 μv rms from 2 Hz to 10 kHz with input shorted;
Calibration: 100 Hz squarewave, 2 μV/div to 10 mV/div in 12 steps;
Electrode impedance check: 1 to 500 kΩ;
Temperature measurement: 200° C. to 400° C.; and
Fully isolated.

Computer 122 is configured to compare an EEG waveform measured from the electrode(s) 180 recording from lateral side 132b to an EEG waveform measured from the electrode(s) 190 recording from contralateral side 136b. Computer 122 compares the SSEP measured in response to stimulation of lateral 132a and contralateral 136a sides of the patient's body to generate an SSEP ratio (which we may refer to as an "ischemia ratio"). The numerator of the ratio can be the amplitude or latency of the SSEP measured from the side of the brain suspected of having ischemia, and the denominator of the ratio can be the amplitude or latency of the SSEP measured from the contralateral side of the brain. The computer 122 can provide a user interface to input which side of the patient's brain (the left or right) is suspected of being ischemic. Alternatively, the computer 122 may allow a user to indicate which side of the patient's body is affected by a symptom of a stroke, such as numbness, tingling, or pain, and the computer will then make a determination as to which side of the brain is suspected of containing ischemic tissue. Computer 122 may include commercially available software useful for processing and presenting the ischemia ratio data, such as the Viking EMG, or EP software packages available from Nicolet Biomedical (Madison, Wis.).

The raw EEG measurement data and any data generated by the computer may be stored for later retrieval.

In system 110, computer 122 is connected to the stimulator 114 by connector 115. The connector 115 can be a wire cable, coaxial cable, optical cable, fiber optic cable, infrared connection, or the like. The connector 115 can be attached to each of the stimulator 114 and the computer 122 by an appropriate coupling or adaptor, including, but not limited to a BNC connector, banana jack, phone connector, D-shell connector, cable connector, coax connector, or alligator clamp. Alternatively, the connector may be permanently operably connected to either the stimulator 114 or the computer 122 by solder or other electrically conductive weld. The connection 115 permits the stimulator 114 to trigger the measurement of an SSEP (i.e., the computer 122 can be programmed to control the initiation of the stimuli). Thus, each time the stimulator 114 generates an stimulus to the lateral 132a and/or contralateral 136a areas of the patient's body, an electrical signal is transmitted to the computer 122 that permits recording and storage of data resulting from the SSEPs transmitted by electrodes 180 and 190. Thus, the computer 122 can synchronize the stimuli provided to the lateral 132a and contralateral 136a structures with the response signals received via recording electrodes 180 and 190.

The SAC device 118 is connected via connector 117 to the computer 122, which permits the electrical signal received from the recording electrodes 180 and 190 to be transmitted to the computer 122. Connector 117 may be identical or substantially identical to connector 115 and/or to connectors 119 and 121. More generally, two or more of the connectors of system 110 can be identical or substantially identical and can be an analog cable, a digital cable, a coaxial cable, a fiber optic cable, a telephone cable, or any other material capable of conducting a signal from one component of system 110 to another.

Where the computer 122 is not remote from the indicator 126, such that both the computer 122 and the indicator 126 are incorporated into the same device by way of a housing, case, shell, frame, or other suitable mechanism, packaging, or confinement, the connector 119 may be a solder or other electrically conductive weld.

System 110 can determine both an afferent and an efferent neuronal integrity by determining the time required to conduct an electrical signal from the brain to peripheral structures, the time required to conduct an electrical signal from peripheral tissues back to the brain, and the amplitude of the electrical signal received by either the brain or the peripheral structure (e.g., a muscle). In accordance with the teaching above, either or both of these values (time and amplitude) can be compared between the lateral and contralateral sides of the patient's body to detect ischemia in the brain (e.g., ischemia in the left or right hemisphere). Ischemia is likely to be present when the amplitude and/or latency of the response differs between the two sides of the brain or when the amplitude and/or latency of the response differs from an established reference standard. For example, where the left hand side of the brain (which can be arbitrarily designated the lateral side of the brain) is ischemic, the amplitude of the SSEPs it generates will be less than the amplitude of the non-ischemic right hand side of the brain (which can be arbitrarily designated the contralateral side of the brain). As noted above, the amplitudes of the SSEPs can be expressed as a fraction or ratio. Where $\text{Amplitude}_L:\text{Amplitude}_R=0.5:1.0$ (or ½, or any value less than 1.0), the left hand side of the brain is likely to be ischemic relative to the right hand side of the brain. Similarly, where the left hand side of the brain is ischemic, the latency of the response it generates will be longer than the latency of the response generated by the non-ischemic right hand side of the brain. Latencies can also be expressed as a fraction or ratio. For example, where $\text{Latency}_L:\text{Latency}_R=5.0:1.0$ (or 5, or any value greater than 1.0 (e.g., a value of about 1.2, 1.3, 1.4, 1.5, 1.7, 2.0, 2.5, 3.0, 3.5, 4.0, 5.0 or more), the left hand side of the brain is likely to be ischemic relative to the right hand side of the brain.

EEG waveform activity can be measured before, during, and after repetitive stimulation. Although EEG recordings permit examination of both cortical and subcortical processing of afferent sensory information, examination of cortical processing may be most useful in detecting and assessing ischemia.

Assessing Ischemia with TMS: Referring to FIG. 6, an ischemia detection system 210 uses TMS, which reflects the integrity of efferent neuronal pathways, to assess ischemia. TMS of the motor cortex can evoke D-waves, representing direct stimulation of the corticospinal axon, I-waves, which arise from the transsynaptic activation of corticospinal neurons, as well as a measurable motor unit potential that can be recorded from a peripheral structure. TMS may also produce actual muscle movement that can be evaluated as a measure of brain damage or ischemia. Thus, the systems and methods of the invention can be configured to assess electrical potentials or physical movement in response to TMS. Where an electrical potential is assessed, that potential can be a "motor unit potential," which is electrical potential (change in voltage) measurable in a muscle that represents depolarization or hyperpolarization of one or more muscle cells. While any change in potential may be significant, detectable and significant changes in response to a stimulus are likely to be at least +/−0.4 mV. System 210 includes a cortical stimulator 214, a SAC device 218, a computer 222 and an indicator 226.

Cortical stimulator 214 exposes the left and right hemispheres of a patient's brain 232a and 232b, or portions thereof, to electromagnetic stimulation by producing a high intensity magnetic field pulse suitable for neurophysiological applications. With respect to specific properties: cortical stimulator 214 includes a capacitor discharge system having a working voltage of between 500 and 4000 V and capable of storing energy levels of between 400 and 2000 J; produces a magnetic field of up to and including 2.5 Tesla, with a magnetic field rise time of between 50 and 200 μs into a magnetic coil 265 having an outside diameter of 50 to 150 mm; delivers magnetic impulses of between 1 and $2.5 \times 10^5$ Gauss, or about 1 to 2.5 Tesla; and provides a magnetic flux stimulus to the brain of a patient of at least about 100 mA (e.g., 90–150 mA) for a duration of between about 0.1–10 ms (e.g., about 0.5, 1.0, 1.5, 2.5, 5.0 or 7.5 ms).

Cortical stimulator 214 can be a monophasic or near-monophasic, stimulator that induces currents that rise to peak levels over 5 μsec, or less, and that then rapidly decay to zero over a time of about 100 μs. Alternatively, a cortical stimulator 214 can be a biphasic or polyphasic stimulator that delivers two or more oscillatory current phases into the brain of a patient. The cortical stimulator 214 may be operably connected to a switch (not shown), such as a foot switch, a push button, a lever, or the like that can be used to trigger the discharge of the magnetic capacitor in the cortical stimulator 214. Any of the stimulators used in the context of the present invention can be similarly controlled.

Magnetic coil 265 can contain between about 10 and 1000 windings of wire that store and discharge a magnetic current. A magnetic coil 265 may be obtained from commercial sources such as, but not limited to, Medtronic (North MSX180 Shoreview, Minn.), and can be variously configured as a standard coil, a figure-8 coil, a butterfly coil, an angled coil, a small round coil, or a cone coil.

System 210 relies on the detection of peripheral responses to cortical stimulation. As in other configurations, the signals generated can be detected by electrodes 280 and 290 on the lateral and contralateral sides of the patient's body. Electrodes 280 and 290 can record, for example, motor unit potentials from peripheral tissues 232b and 236b on the lateral and contralateral sides of the patient's body. The electrodes 280 and 290 can be removable surface electrodes (having, for example, an adhesive surface); parallel bar electrodes; or needle electrodes. As noted above, such electrodes are known in the art and are commercially available from, for example, Delsys (Boston, Mass.) and Rochester Electro-medical (Tampa, Fla.). The peripheral tissues from which electrodes 280 and 290 record can vary greatly and include muscles of the arms and hands, legs and feet, torso, and face. In one example, recording electrodes 280 and 290 measure motor unit potentials from the opponens pollicis. The electrodes 280 and 290 may each be a plurality of electrodes, which can be used to record motor unit potentials in different muscles or at different anatomical or functional locations within a single muscle or within more than one muscle. Alternatively, the electrodes 280 and 290 can each be a single electrode.

In system 210, recording electrodes 280 and 290 are operably connected to the SAC device 218 by the connector 223. As in other embodiments, and as with other connectors of system 210, the connector 223 can be an analog cable, a digital cable, a fiber optic cable, a telephone cable, an infrared connection, or other material capable of conducting a signal from the electrodes 280 and 290 to the SAC device 218 (or between other components of the systems described herein). Similarly, connector 223 can be connected to the recording electrodes 280 and 290 and the SAC device 218 by any suitable coupling or adaptor known in the art (e.g., a BNC coupling, banana jack, phone coupling, multi-pin coupling, D-shell coupling, cable coupling, coax coupling, alligator clamp, solder or other electrically conductive weld). Such couplings or adaptors are suitable for use in connection with any of the connectors of system 210.

In one example, the electrodes 280 and 290 are used to record either a motor unit potential or a D-wave, in which case the SAC device 218 can be set to filter the signal received from electrodes 280 and 290 via filter 228, generally at a low frequency of about 2.0 Hz and a high frequency of approximately 15 kHz. The specific filtering parameters may vary with particular recording scenarios, and one of skill in the art would be able to adjust the filter settings accordingly. The SAC device 218 can also contain an amplifier 229 to amplify the signals received and improve the signal-to-noise ratio (data may be averaged over several stimulus/response phenomena to enhance the signal-to-noise ratio) and an A/D converter 230.

The SAC device 218 is, in turn, operably connected to a computer 222 by connector 217, which permits the electrical signal received from the electrodes 280 and 290 and processed by the SAC device 218 to be transmitted to the computer 222. Connector 217 may be identical to connector 117. Alternatively, the SAC device 218 and computer 222 may be incorporated into a single device or be closely connected by a solder, electrically conductive weld, or printable circuit. SAC device 218 and computer 222 can be incorporated into a single device by way of a housing, case, shell, frame, or other suitable mechanism. The same is true for any of the SAC devices and computers within the systems of the present invention.

Computer 222 is configured to compare any response (e.g., motor unit potential) recorded by the first set of electrodes 280 to a similar response (e.g., motor unit potential) recorded by the second set of electrodes 290. Responses such as muscle movement can be recorded differently, for example, by physical measurement and input by a user into computer 222. More specifically, a user can measure the deflection of a muscle by, for example, a force transducer, a measuring tape, or other suitable measuring device and manually input the measurement, or a representation thereof, into the computer 222. Where the deflection measuring device produces an electronic measurement, that measurement can be inputted directly into the computer 222 by a connector.

Regardless of the source of the data, computer 222 can perform a comparison of the response generated on one side of the patient's body (e.g., the side designated the lateral side 232b) with the response generated on the opposite side of the patient's body (e.g., the side designated the contralateral side 236b). For example, D-wave amplitude, motor unit potential, or physical movement measured in response to stimulation of the lateral 232a or contralateral 236a sides of the cortex can be compared to generate a fraction or ratio (which may be referred to as a "TMS ischemia ratio"). In keeping with other systems described herein, the numerator of the ratio can be the D-wave amplitude, motor unit potential, or physical movement measured on one side of the body (as opposed to one side of the brain), and the denominator of the ratio can be the D-wave amplitude, motor unit potential, or physical movement measured on the contralateral side of the body (preferably at a location that is roughly symmetrical, about the midline, to the first location). Ischemia is determined to be present if the TMS ischemia ratio is different from about 1.0:1.0 (or the "final" value is a value other than 1.0). The computer 222 can provide a user interface to input which side of the patient's brain (the left or right) is suspected of being ischemic. Alternatively, the computer 222 may allow a user to indicate which side of the patient's body appears to be affected by a symptom of a stroke. Computer 222 may include commercially available software, such as that described above. The raw data (e.g., motor unit potential data), as well as the fraction, ratio, or other figure (e.g., "final" value) produced can be stored in the computer 222 for later retrieval.

Typically, up to about 200 stimuli/recording phenomena (e.g., about 2, 4, 6, 8, 10, 40, 50, 100, or 200 stimuli/recording phenomena) are obtained from each side of the brain/periphery and averaged by the computer 222. In general, expected motor unit potential (depolarization) values measured in response to TMS stimulation are approximately 8–11 mV in amplitude, and have a duration of between about 9 and 10 ms.

Indicator 226 indicates a representation of the calculated TMS ischemia ratio. The indicator 226 is further operably connected to the computer 222 via a connector 219, which may be the same type of connector as connector 119. Similarly, the indicator 226 may be the same as (or essentially the same as) indicator 126. The indicator 226 may be remote from the computer 222 or integrated with or within the computer 222 (e.g., within the same housing, case, shell, frame, or the like).

In system 210, the computer 222 is connected to the cortical stimulator 214 by connector 215, which may be a wire cable or any of the materials described above, and which can be attached to each of the cortical stimulator 214 and the computer 222 by a BNC connector or any of the connectors or adaptors listed above. Alternatively, the connector can be essentially permanently and operably connected to either or both of the stimulator 214 and the computer 222 by, for example, by solder or other electrically conductive weld. The connector 215 permits the cortical stimulator 214 to trigger the measurement of a peripheral signal (e.g., a motor unit potential) via the recording electrodes 280 and 290; that is, each time the cortical stimulator initiates a magnetic pulse to the lateral 232a or contralateral 236a side of the brain of a patient, an electrical signal is transmitted, via the SAC device 218, to the computer 222, which records and optionally stores the resulting measurement.

As described above for SSEP based ischemia detection, the TMS-based system 210 can be used to determine the integrity of the regional blood supply to the brain or to assess ischemia within a given vascular field. Using a TMS-based system, it is the sites at which the responses are recorded that correspond to a particular vascular distribution. For example, recording a motor unit potential from the leg will be indicative of the integrity of the ACA; recording from the arm or hand will be indicative of the integrity of the MCA; and recording from the face will be indicative of the integrity of the PCA. Thus, a user can determine the integrity of the PCA, MCA, and ACA (or assess ischemia within the tissue these vessels supply) by stimulating the motor cortex using TMS and recording (sequentially or simultaneously) bilateral motor responses from the foot, hand, and face, respectively.

Assessing Ischemia using NIRS: Referring to FIG. 7, an ischemia detection system 310 assesses ischemia using NIRS, a technique that can be used to monitor local changes in cerebral oxygenation and hemodynamics during functional brain activation. NIRS uses low levels of optical radiation that can penetrate the outmost several centimeters of brain tissue (e.g., optical radiation having a wavelength of about 650 to 950 nm (e.g., 500–1200 nm)). As a result, a user can non-invasively probe the cortex of the brain and monitor the concentration of various species of hemoglobin (a dominant near-infrared absorbing molecule). In particular, two species of hemoglobin—HbO and Hb—have different near-infrared absorption spectra and can be measured separately with NIRS. As the concentrations of these molecules vary depending on, for example, regional blood volume, blood flow, and metabolic oxygen, and accurate measurements of HbO and Hb can be made using light of two wavelengths, the relative amounts of these species of hemoglobin can be assessed in the context of the present invention as an indication of ischemic tissue.

Stimulating peripheral structures that are innervated by nerves extending from distinct vascular territories in the brain and measuring the resulting change in the HbO:Hb ratio for each territory allows one to assess the vascular integrity of the ACA, MCA, and PCA and to determine whether there is ischemia in the vascular fields they supply. The stimuli can be provided (sequentially or simultaneously) to, for example, the peroneal nerve, median nerve, and auditory nerve, in which case the resulting HbO:Hb levels will reflect the integrity of the ACA, MCA, and PCA respectively.

System 310 includes a stimulator 314, a SAC 318, a computer 322, and an indicator 326. The components of the system 310 conform to those of system 10 and to the specific systems exemplified above (110 and 210). For example, the connectors and the indicator of system 10, in any of their various configurations, can be a part of system 310. In system 310, however, while a stimulus may be used (e.g., a stimulus to a peripheral nerve or sensory organ), it is not required.

Figure 8:
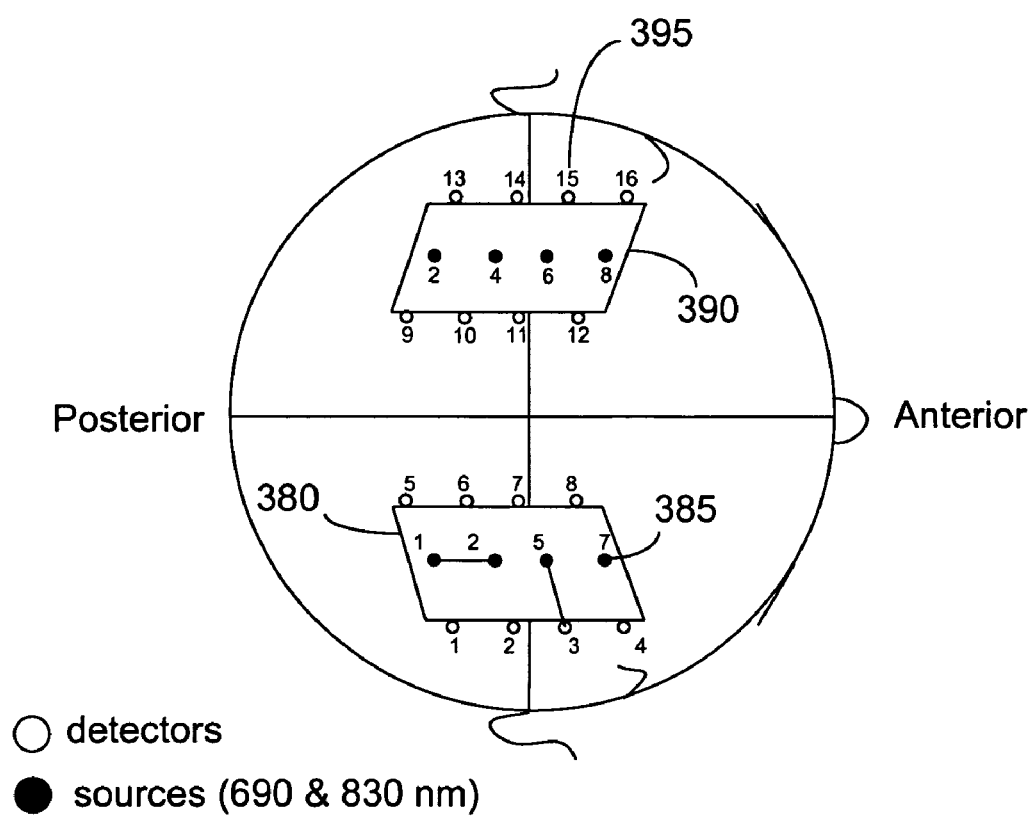
FIG. 8 is a diagram of detectors used the course of detecting ischemia using the NIRS technique.

Referring to FIG. 8, the detectors 380 and 390 include laser diodes 385 and avalanche photodiode detectors 395. The detectors 380 and 390 are capable of generating near infrared optical radiation of between about 650 and 950 nm, where, as noted above, the relatively low attenuation of light accounts for an optical penetration through several centimeters of tissue. The detectors 380 and 390 include between about 1 and 30 diode/detector pairs. In one example, the detectors 380 and 390 each contain 16 laser diodes and sixteen avalanche photodiode detectors (Hamamatsu C5460-01). The laser diodes 385 are adapted to emit light at between about 650 and 950 nm and are frequency encoded by steps of approximately 200 Hz between 4.0 kHz and 8 kHz, so that their signals can be acquired simultaneously by the corresponding photodiode detector 395. The output from the photodiode detector 395 is digitized at between 20 and 50 Hz, and can be filtered using an infinite-impulse-response filter with a band pass frequency of about 20 Hz (e.g., the filter 328 present in the SAC device 310).

The detectors 380 and 390 are placed on the scalp of a patient, generally on the areas overlying the primary sensory cortex. In one example, a Hbo:Hb ratio is generated from between 2 to 500 repetitive stimulus/recording events, the results from which are input into the computer 322, and averaged.

The computer 322 is adapted to measure the concentrations of HbO and Hb. Changes in the intensity of the near-infrared signal are translated into temporal changes in the absorption coefficient $\Delta\mu\alpha$, using the differential-path-length-factor method (DPF). Based on the value of $\Delta\mu\alpha$, the computer is able to determine the changes in HbO and Hb concentrations and calculate a Hbo:Hb ratio.

In one example, the present invention provides methods of detecting ischemia in a patient's brain by providing a first NIRS signal (e.g., an HbO:Hb ratio) from the left-hand side of the patient's brain; providing a second NIRS signal from the right-hand side of the patient's brain (where the first signal is an HbO:Hb ratio, the second signal will also be an HbO:Hb ratio); and comparing the first and second NIRS signals to generate a fraction or ratio. The first and second signals can be obtained from regions of the brain that are located symmetrically about the midline, and the signals can be obtained (but are not necessarily obtained) following a specific peripheral stimulus (e.g., any of the mechanical or sensory stimuli described above). As many of the nerve pathways cross the midline (so that a stimulus applied to the left side of the body produces a response within the right side of the brain and vice versa), in this embodiment and others described herein, a user will provide a stimulus to a tissue on one side of the body and record a response on the other side (the contralateral side) of the body. As in other embodiments, the ratio will include a denominator that can be the value of the first NIRS measurement, in which case the numerator will represent the value of the second NIRS measurement. Where the ratio is different from 1.0:1.0, the ratio indicates the presence of ischemic tissue.

Alternatively, and for example, computer 322 collects data that includes HbO:Hb values obtained from bilateral hemispheres of the patient's brain in response to bilateral stimulation of peripheral structures as follows:

1. Stimulate a lateral peripheral structure and measure HbO:Hb on the contralateral side of brain. If the contralateral side has HbO:Hb>1 then no ischemia. If the contralateral side has HbO:Hb$\leq$1 then ischemia in the contralateral side. Confirmation is made by measuring HbO:Hb in the lateral side of brain. If the contralateral and lateral side of the brain has HbO:Hb>1 then no ischemia. If contralateral side has HbO:Hb$\leq$1 and lateral side has HbO:Hb>1 then ischemia is confirmed in the contralateral side of the brain.
2. Stimulate the contralateral side structure and measure HbO:Hb on the lateral side of brain. If the lateral side has HbO:Hb>1 then no ischemia. If the lateral side has HbO:Hb$\leq$1 then ischemia in the lateral side of the brain. Confirm by measuring HbO:Hb in the contralateral side of brain. If the lateral and the contralateral HbO:Hb>1 then no ischemia. If lateral HbO:Hb$\leq$1 and contralateral HbO:Hb>1 then confirmed ischemia in the lateral brain.

Other embodiments: The systems, processes, and methods of the present invention are not limited to the specific examples described above. More specifically, and for example, the processes illustrated in FIGS. 2 and 4 can be altered by re-ordering, omitting, or repeating one or more of the process steps, as necessary or desired, to achieve the results set forth above (e.g., to rapidly detect and/or assess ischemia within the brain). Similarly, the steps of the processes can be carried out with hardware or software other than that illustrated in FIG. 3. For example, the processes of the invention can be executed in any computing or processing environment and with any type of machine that is capable of running a computer program. The methods can be implemented using hardware, software, or a combination of the two. For example, the systems described herein can be implemented in a circuit that includes one or a combination of a processor, a memory, programmable logic, and logic gates. The processes can be implemented using computer programs executed on programmable computers/machines that each includes a processor, a storage medium or other article of manufacture that is readable by the processor (including, for example, volatile and non-volatile memory and/or storage elements), at least one input device, and one or more output devices. Program code may be applied to data entered using an input device to perform the processes and to generate output information.

Each such program can be implemented in a high level procedural or object-oriented programming language to communicate with a computer system. However, the programs can be implemented in assembly or machine language. The language may be a compiled or an interpreted language. Each computer program may be stored on a storage medium or device (e.g., a CD-ROM, hard disk, or magnetic diskette) that is readable by a general or special purpose programmable computer/machine for configuring and operating the computer when the storage medium or device is read by the computer to perform the processes. The invention may also be implemented as a machine-readable storage medium, configured with a computer program where, upon execution, instructions in the computer program cause the computer to operate in accordance with the processes.

The size of the physical components of the systems may vary as well. For example, system 10 can be constructed in miniature or using sufficiently small components that it can be transported from place to place. The SAC device 18, the computer 22, the indicator 26, and the stimulator 14 may all be incorporated into a single device similar in size to a cellular telephone, personal digital assistant (PDA) or to a laptop computer. Alternatively, the cellular telephone, PDA, or laptop computer may be adapted to function as the computer 22 and further adapted to include the SAC device 18, the stimulator 14, and the indicator 26. Of course, the computer 22, the indicator 26, the SAC device 18, and the stimulator 14 may be encased in a single device that is similar in size to a conventional desktop computer or may be contained within a single device having a size intermediate between those of a cellular telephone, PDA, laptop computer, and desktop computer. While the systems of the present invention may be contained in devices larger than a desktop computer, such configurations would likely lose the advantage of ready portability. The computer 22 may be considered a general purpose or special purpose computer (e.g., controller, digital signal processor, and so forth).

The components of system 10, whether contained in a single housing or not (one or more of the components may be in remote locations), can be configured to measure or receive data concerning electrical activity within the brain (e.g., SSEPs), the chemical content of the brain (e.g., the ratio of HbO:Hb determined, for example, by NIRS), and/or electrical or physical activity in the periphery of the body (e.g., motor unit potentials and/or D-waves from muscle fibers or muscle movement).

System 10, regardless of the size of the components or their precise configuration, can also include inputs, to which connectors could be operably connected, to permit the computer to control both the stimulator (which can activate any type of electrical, magnetic, or physical stimulus, for example, the magnetic coil depicted in system 210) and any recording devices (e.g., recording electrodes). As described above, system 10 can include outputs to permit the ratios or final values calculated by the computer 22 to be displayed on an indicator, and we note here that the system can include more than one indicator (e.g., an integrated indicator that can be viewed by the user or the patient and a remote indicator that can be viewed by, for example, a health care professional at the remote location). Accordingly, system 10 can include a communication port (e.g., a telephone jack, T1 connection, or Ethernet jack) that is operably connected to a telephone modem, cable modem, or other suitable communication interface, which permits information to be transmitted by, for example, the World Wide Web, an e-mail server, or other internet, Ethernet, or intranet servers.

As the systems of the invention can be used to assess ischemia over time (e.g., constantly or intermittently over a period of hours or days), the stimulator 14 can be one that delivers a stimulus (e.g., an auditory stimulus such as a tone or click (or a series of tones or clicks) at a frequency of between 0.1 and 100 Hz) on a regular basis. Similarly, the indicator 26 can be configured to sound an alarm (e.g., a bell, whistle, or the like) that would be heard at a nursing station or other remote monitoring location. Alternatively, or in addition, indicator 26 may provide a visual signal (e.g., a flashing light), and the alarm may sound when a certain pre-set value, such as a certain ischemia ratio, is calculated by the computer 22. For example, the computer 22 can be programmed such that when an ischemia ratio is not equal to one, an electrical signal is propagated to the indicator, thus producing an alarm. Either the computer 22 or indicator 26 may be programmed such that the output of the indicator (for example, the pitch of the tone, color of the light, or text displayed on a cathode ray tube or LCD screen, for example) varies according to whether the ischemia ratio is less than, greater than, or equal to one.

As noted above, the SAC device 18 can convert a response signal from digital to analog, and it may also be configured to convert an analog signal to a digital signal. Methods and mechanisms for either conversion are known to those of ordinary skill in the art and may be readily incorporated into a SAC device 18. The SAC device 18 and computer 22 can be incorporated into a single device or housing, such that the SAC device 18 and computer 22 are physically attached to one another (e.g., by solder or other conductive weld) or in close proximity to one another (e.g., within the same housing, case, shell, frame, package, or the like). The SAC device may also be incorporated into a single device or housing with the detectors (e.g., electrodes 180 and 190 or NIRS detectors 380 and 390). One of ordinary skill in the art will recognize that other methods of connection and other consolidations of the components of the systems are possible and are within the cope of the present invention.

Electrodes 160 and 170 may be configured in any way to allow the receipt and transmission of an electrical, mechanical, or chemical signal, and they can be removably attached to the skin overlying the lateral and contralateral areas 132*a* and 136*a*, or, in an alternate example, may be a coaxial needle electrode which is inserted through the skin and placed in close proximity or in contact with the lateral and contralateral areas 132*a* and 136*a* which are to be stimulated. Alternatively, the electrodes 160 and 170, may not be electrodes at all, but instead an ear-piece capable of delivering a tone or click when placed in close proximity to the ear of a patient.

In one example, the electrodes 160 and 170 are a plurality of electrodes comprising a lateral and contralateral electrode adapted for providing stimulation to the lateral and contralateral tibial or peroneal nerves, a lateral and contralateral electrode adapted for providing stimulation to the lateral and contralateral median nerves, and a lateral and contralateral electrode (e.g., ear-piece) adapted for providing stimulation to the lateral and contralateral auditory nerves (cranial nerve eight).

The electrodes 180 and 190 may be surface electrodes, which are capable of being removably attached to the scalp of the patient, or, alternatively, the electrodes 180 and 190 may one or a plurality of needle electrodes, which may be used to record an SSEP or EEG waveform directly from the surgically exposed cortex of the patient. In one example, the electrodes 180 and 190 are removably attachable surface electrodes. The electrodes 180 and 190 may be two distinct electrodes or sets of electrodes, or alternatively, electrodes 180 and 190 may be a single array of electrodes which is adapted to be able to record an EEG waveform from either or both of the lateral and contralateral cortex 200 and 210, individually, or simultaneously.

Connector 121 may include, but is not limited to, wire cable, coaxial cable, optical cable, fiber optic cable, and infrared connection. The connector 121 may be attached to each of the electrodes 180 and 190, and the SAC device 118 by an appropriate coupler or adaptor, including, but not limited to a BNC connector, banana jack, phone connector, D-shell connector, cable connector, coax connector, and alligator clamp. Alternatively, the connector may be permanently operably connected to the SAC device 118, or the electrodes 180 and 190, for example by solder or other electrically conductive weld known to those of skill in the art. In this example, the connector 130 may be a solder, or other electrically conductive weld.

The system 10 may be used in a variety of applications. For example, system 10 may be used to test the responsiveness and/or effectiveness of drugs useful in the treatment of stroke (e.g., thrombolytic or embolic stroke). For example, any animal model of stroke can be used in conjunction with one or more of the methods described herein to identify therapeutic agents (from, for example, a compound library or other collection of potential therapeutic agents (e.g., a cDNA library, a peptide library, an siRNA or antisense oligonucleotide library).

Other implementations are within the scope of the following claims.

What is claimed is:

1. A method of detecting ischemia within the brain of a patient, the method comprising:
   applying a first stimulus to the left-hand side of the body;
   assigning a first value to a first signal generated by a tissue on the right-hand side of the body in response to the first stimulus;
   applying a second stimulus to the right-hand side of the body;
   assigning a second value to a second signal generated by a tissue on the left-hand side of the body in response to the second stimulus; and
   comparing the first value and the second value, wherein a difference between the first value and the second value indicates that ischemia is present within the brain.

2. The method of claim 1, wherein the first stimulus or the second stimulus comprises an electrical stimulus.

3. The method of claim 1, wherein the first stimulus or the second stimulus comprises an auditory stimulus or a visual stimulus.

4. The method of claim 1, wherein the first stimulus or the second stimulus comprises a stimulus to the patient's skin or an underlying muscle.

5. The method of claim 1, wherein the first stimulus is applied to a sensory organ on the left-hand side of the body and the first signal is generated by the right hemisphere of the brain.

6. The method of claim 5, wherein the second stimulus is applied to a sensory organ on the right-hand side of the body and the second signal is generated by the left hemisphere of the brain.

7. The method of claim 6, wherein the sensory organ is the eye or ear and the first signal or the second signal is an electrical signal.

8. The method of claim 7, wherein the first electrical signal is a first somatosensory evoked potential (SSEP) and the second signal is a second SSEP.

9. The method of claim 8, wherein the first value is based on an amplitude of the first SSEP and the second value is based on an amplitude of the second SSEP.

10. The method of claim 8, wherein the first value is based on a latency of the first SSEP and the second value is based on a latency of the second SSEP.

11. The method of claim 1, wherein the first stimulus is applied to a nerve innervating a muscle on the left-hand side of the body and the first signal is generated by the right hemisphere of the brain.

12. The method of claim 11, wherein the second stimulus is applied to a nerve innervating a muscle on the right-hand side of the body and the second signal is generated by the left hemisphere of the brain.

13. The method of claim 12, wherein the nerve is the median nerve, ulnar nerve, common peroneal nerve, or posterior tibial nerve.

14. The method of claim 12, wherein the first electrical signal is a first SSEP and the second signal is a second SSEP.

15. The method of claim 14, wherein the first value is based on an amplitude of the first SSEP and the second value is based on an amplitude of the second SSEP.

16. The method of claim 14, wherein the first value is based on the latency of the first SSEP and the second value is based on the latency of the second SSEP.

17. The method of claim 1, wherein the patient is a human patient.

18. The method of claim 1, wherein the first stimulus and the second stimulus are comparable.

19. An article comprising a machine-readable medium that stores executable instructions for detecting ischemia within the brain of a patient, the instructions causing a machine to:
   apply a first stimulus to the left-hand side of the body;
   assign a first value to a first signal generated by a tissue on the right-hand side of the body in response to the first stimulus;
   apply a second stimulus to the right-hand side of the body;
   assign a second value to a second signal generated by a tissue on the left-hand side of the body in response to the second stimulus; and
   compare the first value and the second value, wherein a difference between the first value and the second value indicates that ischemia is present within the brain.

20. The article of claim 19, wherein the first stimulus or the second stimulus comprises an electrical stimulus.

21. The article of claim 19, wherein the first stimulus or the second stimulus comprises an auditory stimulus or a visual stimulus.

22. The article of claim 19, wherein the first stimulus or the second stimulus comprises a stimulus to the patient's skin or an underlying muscle.

23. The article of claim 19, wherein the first stimulus is applied to a sensory organ on the left-hand side of the body and the first signal is generated by the right hemisphere of the brain.

24. The article of claim 23, wherein the second stimulus is applied to a sensory organ on the right-hand side of the body and the second signal is generated by the left hemisphere of the brain.

25. The article of claim 24, wherein the sensory organ is the eye or ear and the first signal or the second signal is an electrical signal.

26. The article of claim 25, wherein the first electrical signal is a first somatosensory evoked potential (SSEP) and the second signal is a second SSEP.

27. The article of claim 26, wherein the first value is based on an amplitude of the first SSEP and the second value is based on an amplitude of the second SSEP.

28. The article of claim 27, wherein the first value is based on a latency of the first SSEP and the second value is based on a latency of the second SSEP.

29. The article of claim 19, wherein the first stimulus is applied to a nerve innervating a muscle on the left-hand side of the body and the first signal is generated by the right hemisphere of the brain.

30. The article of claim 29, wherein the second stimulus is applied to a nerve innervating a muscle on the right-hand side of the body and the second signal is generated by the left hemisphere of the brain.

31. The article of claim 30, wherein the nerve is the median nerve, ulnar nerve, common peroneal nerve, or posterior tibial nerve.

32. The article of claim 30, wherein the first electrical signal is a first SSEP and the second signal is a second SSEP.

33. The article of claim 32, wherein the first value is based on an amplitude of the first SSEP and the second value is based on an amplitude of the second SSEP.

34. The article of claim 32, wherein the first value is based on the latency of the first SSEP and the second value is based on the latency of the second SSEP.

35. The article of claim 19, wherein the patient is a human patient.

36. The method of claim 19, wherein the first stimulus and the second stimulus are comparable.

37. An apparatus comprising
a memory that stores executable instructions for detecting ischemia within the brain of a patient; and a processor that executes the executable instructions to:
apply a first stimulus to the left-hand side of the body;
assign a first value to a first signal generated by a tissue on the right-hand side of the body in response to the first stimulus;
apply a second stimulus to the right-hand side of the body;
assign a second value to a second signal generated by a tissue on the left-hand side of the body in response to the second stimulus; and
compare the first value and the second value, wherein a difference between the first value and the second value indicates that ischemia is present within the brain.

38. The apparatus of claim 37, wherein the first stimulus or the second stimulus comprises an electrical stimulus.

39. The apparatus of claim 37, wherein the first stimulus or the second stimulus comprises an auditory stimulus or a visual stimulus.

40. The apparatus of claim 37, wherein the first stimulus or the second stimulus comprises a stimulus to the patient's skin or an underlying muscle.

41. The apparatus of claim 37, wherein the first stimulus is applied to a sensory organ on the left-hand side of the body and the first signal is generated by the right hemisphere of the brain.

42. The apparatus of claim 41, wherein the second stimulus is applied to a sensory organ on the right-hand side of the body and the second signal is generated by the left hemisphere of the brain.

43. The apparatus of claim 42, wherein the sensory organ is the eye or ear and the first signal or the second signal is an electrical signal.

44. The apparatus of claim 43, wherein the first electrical signal is a first somatosensory evoked potential (SSEP) and the second signal is a second SSEP.

45. The apparatus of claim 44, wherein the first value is based on an amplitude of the first SSEP and the second value is based on an amplitude of the second SSEP.

46. The apparatus of claim 44, wherein the first value is based on a latency of the first SSEP and the second value is based on a latency of the second SSEP.

47. The apparatus of claim 37, wherein the first stimulus is applied to a nerve innervating a muscle on the left-hand side of the body and the first signal is generated by the right hemisphere of the brain.

48. The apparatus of claim 47, wherein the second stimulus is applied to a nerve innervating a muscle on the right-hand side of the body and the second signal is generated by the left hemisphere of the brain.

49. The apparatus of claim 48, wherein the nerve is the median nerve, ulnar nerve, common peroneal nerve, or posterior tibial nerve.

50. The apparatus of claim 48, wherein the first electrical signal is a first SSEP and the second signal is a second SSEP.

51. The apparatus of claim 50, wherein the first value is based on an amplitude of the first SSEP and the second value is based on an amplitude of the second SSEP.

52. The apparatus of claim 50, wherein the first value is based on the latency of the first SSEP and the second value is based on the latency of the second SSEP.

53. The apparatus of claim 37, wherein the patient is a human patient.

54. The method of claim 37, wherein the first stimulus and the second stimulus are comparable.

* * * * *